(12) United States Patent
Shimizu et al.

(10) Patent No.: US 7,683,189 B2
(45) Date of Patent: Mar. 23, 2010

(54) PROCESS FOR PRODUCING AMINOBENZOPYRAN COMPOUND

(75) Inventors: Takanori Shimizu, Funabashi (JP); Hiroo Matsumoto, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 856 days.

(21) Appl. No.: 10/524,686

(22) PCT Filed: Aug. 6, 2003

(86) PCT No.: PCT/JP03/09987

§ 371 (c)(1), (2), (4) Date: Apr. 19, 2005

(87) PCT Pub. No.: WO2004/020428

PCT Pub. Date: Mar. 11, 2004

(65) Prior Publication Data

US 2005/0192444 A1 Sep. 1, 2005

(30) Foreign Application Priority Data

Aug. 29, 2002 (JP) ............... 2002-250112

(51) Int. Cl.
C07D 311/74 (2006.01)
(52) U.S. Cl. .................................... 549/404
(58) Field of Classification Search .................. 549/404
See application file for complete search history.

(56) References Cited

U.S. PATENT DOCUMENTS

| 4,310,527 A | 1/1982 | Jaeggi et al. |
| 6,589,983 B1 | 7/2003 | Tanikawa et al. |

FOREIGN PATENT DOCUMENTS

| EP | 0 488 107 A2 | 6/1992 |
| GB | 1121307 | 7/1968 |
| JP | A 5-78289 | 3/1993 |
| JP | A 2001-151767 | 6/2001 |

| WO | WO 01/85671 A2 | 11/2001 |

OTHER PUBLICATIONS

Evan et al., "Synthesis and Antihypertensive Activity of Substituted trans-4-amino-3,4-dihydro-2,2-dimethyl-2H-1-benzopyran-3-ols," J. Med. Chem, vol. 26, pp. 1582-1589, 1983.
Hine et al., "The Synthesis and Ionization Constants of Some Derivatives of 1-Biphenylenol," J. Org. Chem, vol. 50, 5092-5096, 1985.
Clarke et al., Org. Syn. Coll., vol. 1, pp. 455-457, 1941.
Razafimbelo et al., "Synthesis and Cytotoxic Activity of Pyranophenanthridine Analogues of Fagaronine and Acronycine," Chem. Pharm. Bull., vol. 46, No. 1, pp. 34-41, 1998.
Brown et al., "Studies of Chromenes. Part 10[1] Oxiranes of Nitrochromenes," J. Chem Soc., Perkin Trans, vol. 1, pp. 573-577, 1992.
Gowda S. et al., "Application of hydrazinium monoformate as new hydrogen donor with Raney nickel: a facile reduction of nitro and nitrile moieties," Tetrahedron 58, 2002, pp. 2211-2213.

*Primary Examiner*—Taofiq A Solola
(74) *Attorney, Agent, or Firm*—Oliff & Berridge, PLC

(57) ABSTRACT

There is provided a method for producing aminobenzopyran compound, which results in little wastes, has no influence on reactors and necessitates a simple work-up procedure. Concretely, it is a method for producing aminobenzopyran compound of formula (2)

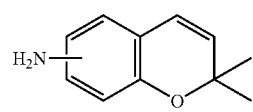

(2)

characterized by reducing a nitro group on 2,2-dimethyl 2H-1-benzopyran compound of formula (1)

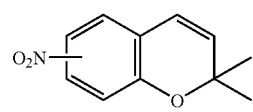

(1)

with hydrazine in the presence of a metal catalyst.

6 Claims, No Drawings

PROCESS FOR PRODUCING AMINOBENZOPYRAN COMPOUND

TECHNICAL FIELD

The present invention relates to a process in which 2,2-dimethyl 2H-1-benzopyran compound having a nitro group on the benzene ring thereof is used and the corresponding aminobenzopyran compound is produced therefrom. Aminobenzopyran compounds are ones useful as intermediates for synthesizing e.g., antifibrillatory agents (see, JP-A-2001-151767) or hypotensive agents (see, J. Med. Chem., 1983, Vol. 26, No. 11, 1582-1589).

BACKGROUND ART

As a method for producing aminobenzopyran compound, there is known a method of reducing the corresponding nitrobenzopyran compound with iron (see, for example GB 1,121,307). The method, however, occurs a large quantity of iron waste and further is liable to do damage to reactors. In addition, the method has disadvantages in procedures (filtration, transfer, stirring or washing), and therefore it has many problems for applying to the production of pharmaceuticals or pharmaceutical intermediates for which a high level of quality control is required. Further, although hydrazine reduction by using $FeCl_3\text{-}6H_2O$ and active carbon as a catalyst (J. Org. Chem., Vol. 50, No. 25, 5092 (1985) and a reduction with tin (Sn)-hydrochloric acid (Org. Syn. Coll., Vol. 1, 455 (1941) are proposed, these methods have problems in aspects of reaction selectivity or toxicity.

If reduction of nitro group is merely required, some methods such as catalytic reduction or the like are known, in which 2,2-dimethyl 2H-1-benzopyran compound being a substrate contains olefin bonds, and it is required to acquire a high selectivity with the bonds. Similarly, a high selectivity with olefin bonds is required in hydrazine reduction by using $FeCl_3\text{-}6H_2O$ and active carbon as a catalyst.

The present inventors, as results of eager investigation, found a method for producing aminobenzopyran compound, which has a high selectivity with olefin bonds, provides intended compounds in a high yield, and further necessitates a simple work-up procedure, results in little wastes and has no influence on reactors, and they consequently completed the present invention.

DISCLOSURE OF THE INVENTION

That is, the present invention relates to a method for producing aminobenzopyran compound of formula (2)

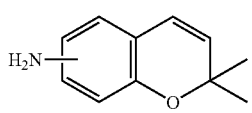
(2)

characterized by reducing a nitro group on 2,2-dimethyl 2H-1-benzopyran compound of formula (1)

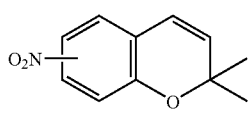
(1)

with hydrazine in the presence of a metal catalyst.

Particularly, the present invention relates to the method for producing aminobenzopyran compound as set forth, wherein 6-amino-2,2-dimethyl 2H-1-benzopyran of formula (4)

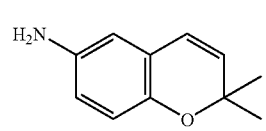
(4)

as aminobenzopyran compound of formula (2) is produced by reducing a nitro group on 2,2-dimethyl-6-nitro 2H-1-benzopyran of formula (3)

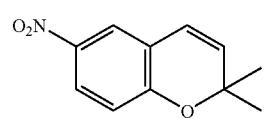
(3)

as 2,2-dimethyl 2H-1-benzopyran compound of formula (1) with hydrazine in the presence of a metal catalyst.

A preferable embodiment of the present invention relates to the method for producing aminobenzopyran compound as set forth, wherein the metal in the metal catalyst is platinum or palladium, and more preferably platinum.

Another preferable embodiment of the present invention relates to the method for producing aminobenzopyran compound as set forth, wherein the hydrazine is used in an amount of 2 to 5 molar equivalents to 1 molar equivalent of 2,2-dimethyl 2H-1-benzopyran compound.

BEST MODE FOR CARRYING OUT THE INVENTION

As metal catalyst, a number of catalyst systems can be used by combining metals used, carriers, additives and the like.

The metals used include platinum, palladium, copper, ruthenium, nickel, an oxide of their metals and an alloy of their metals. Preferable metals used are platinum and palladium, and more preferably platinum.

The carriers include silica gel, alumina, chromium oxide, diatomaceous earth, activated earth, C (active carbon), $BaSO_4$, $CaCO_3$, $SrCO_3$, pumice and several steel shavings, etc.

The additives include $Ba(OH)_2$ and $CaCO_3$, etc.

Concrete catalysts include platinum catalysts such as $PtO_2$, $PtO_2$—C, $PtS_2$, $PtS_2$—C, Pt—C, Pt—S carbon powder and Pt-diatomaceous earth, etc., palladium catalysts such as PdO, palladium black, Pd—C, Pd—$BaSO_4$, Pd—$CaCO_3$, Pd—$SrCO_3$, Pd-silica gel, Pd—$CaCO_3$—$Pd(OAc)_2$ (Lindlar catalyst) and Pd—$BaSO_4$-quinoline, etc., copper catalysts such as Cu—Ba—CrO and Cu—CrO, etc., ruthenium catalysts such as $RuO_2$ and Ru—C, etc., nickel catalysts such as Raney Ni(W1-W8), Ni-diatomaceous earth and Ni-pumice, etc., and the like. The above-mentioned catalysts are appropriately selected according to reactivity, and may be used alone or in an admixture.

Preferable catalysts are Pt—C, Pt—S carbon powder and Pd—C, and more preferably Pt—C.

Used amount of the metal catalyst varies depending on the kind of the catalyst, and is generally 1 to 100 mass % based on 2,2-dimethyl 2H-1-benzopyran compound (1) being raw material, and preferably 3 to 20 mass % from a viewpoint of production cost.

For example, in case where 2% Pt—C (50% water-containing product) is used, it is preferable from a viewpoint of production cost that the catalyst is used in an amount of 3 and 20 mass % (0.03 to 0.2 mass % in the amount of Pt). In addition, for example, in case where 5% Pd—C (50% water-containing product) is used, it is preferable from a viewpoint of production cost that the catalyst is used in an amount of 3 and 20 mass % (0.075 to 0.5 mass % in the amount of Pd).

In the meanwhile, in case where the metal catalyst is water-containing product, the used amount of the catalyst means an amount of water-containing product (that is, an amount of wet product).

Hydrazine used in the present invention is a water-containing product (for example, hydrazine monohydrate, 80% product, etc.) from a viewpoint of chemical safety. The water content is not specifically limited, and it is preferable from viewpoints of production efficiency and prevention of raw material-precipitation that hydrazine monohydrate is used in a concentration of 40 to 98%.

Used amount of hydrazine is generally 0.2 to 20 molar equivalents to 1 molar equivalent of 2,2-dimethyl 2H-1-benzopyran compound (1), and preferably 2 to 5 molar equivalents from viewpoints of safety in handling and production cost.

The solvents used in the reaction are preferably alcoholic solvents such as methanol, ethanol, isopropyl alcohol or the like, ethers that are relatively miscible with water, such as dioxane or tetrahydrofuran. The solvents, however, are not specifically limited thereto. In addition, mixed solvents thereof can be used, and a mixed solvent of methanol and ethanol is preferable.

Used amount of the solvent is preferably 1 to 100 mass times, more preferably 2 to 20 mass times that of 2,2-dimethyl 2H-1-benzopyran compound (1) being raw material.

Reaction temperature is not specified in general as it depends on the kind or used amount of the catalyst. For example, in case where Pd—C is used as metal catalyst, the temperature is generally −20 to 80° C., and preferably 10 to 40° C. from viewpoints of reaction rate and selectivity. In addition, for example in case where Pt—C is used as metal catalyst, the temperature is generally 0 to 120° C., and preferably 30 to 80° C. from viewpoints of reaction rate and selectivity.

Also, reaction time is not specified in general as it depends on the amount of catalyst, the used amount of hydrazine, reaction temperature or the like. Generally, the reaction time ranges from 0.25 to 24 hours.

In the meanwhile, the aminobenzopyran compound of the reaction product can be obtained by filtrating the reaction solution, distilling off the solvent, and then extracting with toluene-water system, and distilling out the solvent of the organic phase again.

In addition, the product can be purified by column chromatography, and further a product obtained by acetylating the amino group thereon can be isolated by crystallization.

In the meanwhile, the metal catalyst used in the method according to the present invention can be recovered in a simple process such as filtration or the like. In addition, as the recovered metal catalyst can be reused, the method of the present invention is a profitable one in the industrial aspect.

Hereinafter, the present invention is concretely described according to examples to which the present invention is not limited.

In the meantime, HPLC relative area percentage was measured under the following analytical condition:

Column: L-Column ODS (manufactured by Chemicals Evaluation Research Institute, Japan);

Development solvent: MeCN: 0.01 M AcONH$_4$ aqueous solution=45:55 (v/v);

UV wavelength: 254 nm;

Flow rate: 1 mumin.;

Column temperature: 40° C.;

Analysis time: 60 minutes.

EXAMPLE 1

Production of 6-amino 2,2-dimethyl 2H-1-benzopyran (4)

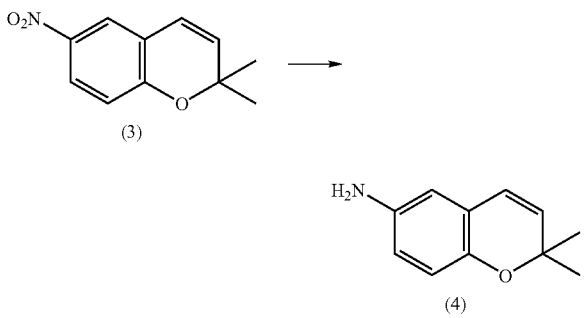

Ten grams (10 g, 48.7 mmol) of 2,2-dimethyl 6-nitro 2H-1-benzopyran (3) was dissolved in 60.0 g of ethanol under heating. After cooling to 35° C., 0.6 g of 2% Pt—C (50% water-containing product) was added thereto, and 5.85 g (117.0 mmol) of hydrazine monohydrate (98% product) was added dropwise (dropwise adding was continued for 30 minutes) while controlling internal temperature to 40° C. or less. After completion of dropwise adding, reaction was carried out at a temperature of 40 to 45° C. for 6 hours. The resulting solution was cooled to room temperature, and then 10.0 g of water was added thereto and the resulting solution was filtered through celite. The celite was washed with 20.0 g of 80% water-containing ethanol, and the washing together with the filtrate were subjected to solvent-distillation. The residue was extracted with 40.0 g of toluene and 20.0 g of water. After separating into phases, the aqueous phase was extracted with 20.0 g toluene again. The toluene phases were combined, washed with 20.0 g of water and then subjected to solvent-distillation to obtain a crude product of intended product (4).

In the meantime, a crude product of 6-amino 2,2-dimethyl 2H-1-benzopyran separately synthesized according to the similar procedure was purified with silica gel chromatography (eluent: ethyl acetate/n-hexane=1/1 (v/v)) and the following physical properties were obtained by use of the resulting product:

Appearance: yellow oil $^1$H-NMR (CDCl$_3$) δ: 1.40 (6H, s), 3.36 (2H, br s), 5.61 (1H, d, J=9.6 Hz), 6.24 (1H, d, J=9.6 Hz), 6.38 (1H, d, J=2.8 Hz), 6.48 (1H, dd, J=2.8 Hz, 8.3 Hz), 6.62 (1H, d, J=8.5 Hz)

MS (m/z); 175 (M+), 160 (M-NH).

REFERENTIAL EXAMPLE 1

Production of 6-acetoamino 2,2-dimethyl 6-2H-1-benzopyran

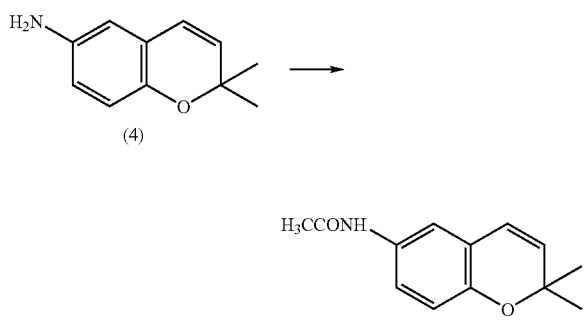

Whole amount of the crude product obtained in Example 1 was dissolved in 30 g of toluene, and 5.10 g (49.7 mmol) of acetic anhydride was added dropwise thereto over 6 minutes (internal temperature: 20 to 26° C.). One hour later, the resulting mixture was subjected to hot-extraction with 30.0 g of toluene and 37.0 g of 8% (w/w) sodium carbonate aqueous solution. The organic phase was subjected to hot-washing with 22.0 g of water, and after distilling off the solvent under a reduced pressure, crystallization gave 10.27 g of the intended product (yield: 97.0%, total yield in two steps of Example 1 and Referential Example 1).

Appearance: white crystal mp: 127.5 to 127.7° C.

$^1$H-NMR (CDCl$_3$) δ: 1.40 (6H, s), 2.09 (3H, s), 5.60 (1H, d, J=9.9 Hz), 6.22 (1H, d, J=9.9 Hz), 6.68 (1H, d, J=8.7 Hz), 7.08 (1H, dd, J=2.4 Hz, 8.4 Hz), 7.23 (1H, d, J=2.7 Hz), 7.93 (1H, br).

EXAMPLE 2

Production of 7-amino 2,2-dimethyl 2H-1-benzopyran

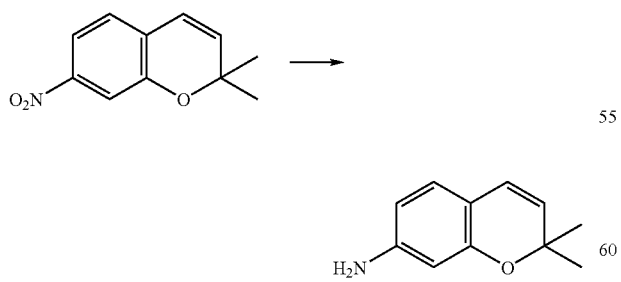

By using 1.00 g (48.7 mmol) of 2,2-dimethyl 7-nitro 2H-1-benzopyran, a crude product of the intended product was obtained in a similar procedure as that in Example 1.

REFERENTIAL EXAMPLE 2

Production of 7-acetoamino 2,2-dimethyl 6-2H-1-benzopyran

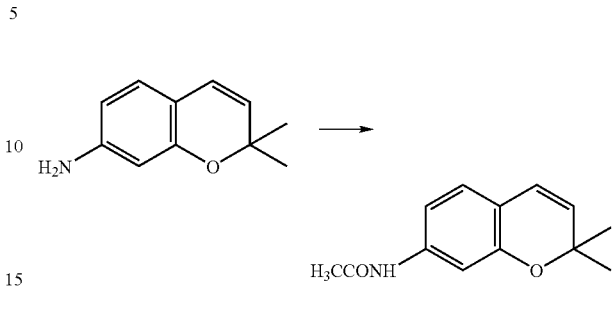

After performing a similar procedure as that in Referential Example 1, a purification was carried out with silica gel chromatography (eluent: ethyl acetate/n-hexane=1/1 (v/v)) to obtain 1.03 g of the intended product (yield: 97.3%, total yield in two steps of Example 2 and Referential Example 2.

Appearance: pale yellow oil $^1$H-NMR (CDCl$_3$) δ: 1.41 (6H, s), 2.13 (3H, s), 5.53 (1H, d, J=9.6 Hz), 6.26 (1H, d, J=9.6 Hz), 6.88 (1H, d, J=7.8 Hz), 6.99 (1H, d, J=8.1 Hz), 7.01 (1H, s), 7.54 (1H, br).

EXAMPLES 3 to 20

In case where compound of formula (3) (0.5 g) was used as raw material and the kind and used amount of metal catalyst, the kind and used amount of hydrazine, the kind and used amount of solvent, reaction temperature, reaction time or the like were varied, the proportion of raw material (3), product (4) and by-products (5) was measured and shown in HPLC relative area percentage.

In the meanwhile, the kind of metal catalyst, the kind of hydrazine and the kind of solvent were shown in the following abbreviation.

Further, the used amount of metal catalyst was shown in mass % based on that of the raw material (in case of water-containing product, amount in a state containing water), the used amount of hydrazine was shown in molar equivalent based that of the raw material, and the used amount of solvent was shown in mass times as that of the raw material.

The kind of metal catalyst
A: 5% Pd—C (50% water-containing product)
B: 2% Pt—C (50% water-containing product)
C: 3% Pt—S carbon powder (65% water-containing product) (manufactured by N.E. Chemcat Corporation)

The kind of hydrazine
D: hydrazine monohydrate (80% product)
E: hydrazine monohydrate (98% product)

The kind of solvent
F: ethanol
G: ethanol/1,4-dioxane=3/1 (v/v)
H: ethanol/water=5/1 (v/v)
I: isopropanol
J: ethanol/1,4-dioxane=1/1 (v/v)
K: ethanol/1,4-dioxane=1/3 (v/v)

Further, in Example 4, after subjecting to reaction at 4° C. for 3 hours, further reaction was carried out at 23° C. for 3 hours and the proportion of the above-mentioned compounds was measured and shown in HPLC relative area percentage.

In the meanwhile, by-product (5) had the structure shown below:

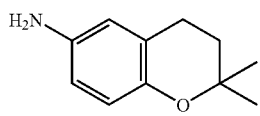

(5)

The results were shown in Table 1.

To the solution, 120 g of toluene was added, and 20.4 g (20.0 mmol) of acetic anhydride was added dropwise at an internal temperature of 20 to 30° C. After stirring for 1 hour, 120 g of toluene and 8% (w/w) sodium carbonate aqueous solution were added dropwise, and the resulting mixture was subjected to hot-extraction at 40° C. Further, water (88 g) was added thereto and the resulting mixture was subjected to hot-washing, and concentrated until the amount of the residue was decreased to 160 g. The residue was subjected to crystallization under ice cooling for 3 hours, then filtered and dried at 60° C. under a reduced pressure to obtain 6-acetoamino 2,2-dimethyl 6-2H-1-benzopyran ACB. Resulting amount: 35.2 g, Yield: 83.2%, Purity: 92.4%.

TABLE 1

| Example No. | Catalyst | | Hydrazine | | Solvent | | Temperature (° C.) | Time (hr) | Proportion (%) | | |
|---|---|---|---|---|---|---|---|---|---|---|---|
| | Kind | Amount | Kind | Amount | Kind | Amount | | | (3) | (4) | (5) |
| 3 | A | 10 | D | 2.0 | F | 12 | 20-23 | 12 | 2.1 | 94.7 | 3.0 |
| 4 | A | 10 | D | 2.0 | F | 12 | 4 | 3 | 87.3 | 3.7 | 0.2 |
| | | | | | | | 23 | 3 | 2.5 | 94.6 | 2.3 |
| 5 | A | 10 | D | 2.0 | G | 12 | 20 | 12 | 4.9 | 92.5 | 1.7 |
| 6 | B | 10 | D | 2.4 | F | 12 | 50-55 | 20 | 6.7 | 92.8 | 0.1 |
| 7 | B | 10 | D | 2.9 | F | 12 | 50-55 | 3 | — | 98.9 | 0.6 |
| 8 | B | 7.5 | D | 2.4 | F | 9 | 50-55 | 3 | — | 99.3 | 0.2 |
| 9 | B | 5 | D | 2.4 | F | 6 | 50-55 | 6 | — | 99.1 | 0.2 |
| 10 | B | 4 | D | 2.4 | F | 4 | 50-55 | 3 | — | 99.0 | 0.4 |
| 11 | B | 6 | D | 2.4 | H | 6 | 50-55 | 6 | 1.5 | 96.9 | 0.3 |
| 12 | B | 6 | D | 2.4 | I | 6 | 50-55 | 6 | — | 99.2 | 0.6 |
| 13 | B | 6 | D | 2.4 | G | 6 | 50-55 | 6 | 0.3 | 99.1 | 0.1 |
| 14 | B | 6 | D | 2.4 | J | 6 | 50-55 | 6 | — | 99.1 | 0.5 |
| 15 | B | 6 | D | 2.4 | K | 6 | 50-55 | 6 | — | 99.4 | 0.2 |
| 16 | B | 6 | D | 2.4 | F | 6 | 40-45 | 6 | — | 99.4 | 0.1 |
| 17 | B | 6 | D | 2.4 | G | 6 | 40-45 | 6 | — | 99.4 | 0.1 |
| 18 | B | 6 | D | 2.4 | G | 6 | 35-40 | 9 | — | 99.3 | 0.1 |
| 19 | B | 6 | E | 2.4 | G | 6 | 40-45 | 6 | — | 99.5 | 0.2 |
| 20 | C | 10 | D | 3.8 | F | 12 | 50-55 | 9 | — | 99.0 | 0.5 |

COMPARATIVE EXAMPLE 1

Example of Reduction by Use of Iron 2,2-dimethyl 6-nitro 2H-1-benzopyran (3), 40.1 g (185 mmol) was mixed with 120 g of ethanol, 28.0 g of water and 36.1 g of reduced iron, the resulting mixture was heated to 60° C., and a mixed solution of 4.0 g of 35% (w/w) hydrochloric acid, 16.0 g of ethanol and 4.0 g of water was added dropwise thereto over 50 minutes. After stirring at the same temperature for 2 hours, 10.0 g of 15% (w/w) sodium hydroxide aqueous solution was added dropwise thereto, the resulting mixture was filtered through celite, and then the solvent was distilled off. To 112 g of the resulting residue, 160 g of toluene and 68.0 g of 10% (w/w) sodium hydroxide aqueous solution were added, the resulting mixture was shaken, left and separated into phases. The aqueous phase was extracted with 68 g of toluene again. The organic phases were combined and washed with 68 g of 5% (w/w) sodium chloride solution, and the solvent was distilled off to obtain a solution of the intended product, 6-amino 2,2-dimethyl 6-2H-1-benzopyran (4) (68.0 g).

COMPARATIVE EXAMPLES 2 TO 7

Examination of Hydrogen Source Other than Hydrazine

In case where the compound (3) (0.5 g) was used as raw material and hydrazine was replaced with other hydrogen source, the proportion of raw material (3), product (4) and by-product (5) was measured and shown in HPLC relative area percentage.

In the meanwhile, the abbreviation and unit in Table 2 are the same as those in Table 1.

In addition, the kind of hydrogen source were shown in the following abbreviation.

The kind of hydrogen source:

L: hydrogen gas (ordinary pressure: $H_2$ balloon)

M: ammonium formate

The results were shown in Table 2.

TABLE 2

| Comparative Example No. | Catalyst Kind | Catalyst Amount | Source of Hydrogen Kind | Source of Hydrogen Amount | Solvent Kind | Solvent Amount | Temperature (°C.) | Time (hr) | Proportion (%) (3) | (4) | (5) |
|---|---|---|---|---|---|---|---|---|---|---|---|
| 2 | A | 10 | L |  | F | 12 | 15-20 | 12 | — | — | 91.9 |
| 3 | A | 10 | M | 4.0 | F | 12 | 15-20 | 12 | — | — | 98.7 |
| 4 | A | 10 | M | 1.2 | F | 12 | 15-20 | 12 | 83.9 | 12.7 | 3.2 |
| 5 | C | 10 | L |  | F | 15 | 15-20 | 4 | 8.1 | 63.6 | 20.4 |
| 6 | C | 10 | L |  | F | 15 | 15-20 | 8 | 0.42 | 29.5 | 61.3 |
| 7 | C | 10 | L |  | F | 15 | 15-20 | 30 | — | — | 91.9 |

COMPARATIVE EXAMPLE 8

Reduction with hydrazine was attempted by using $FeCl_3 \cdot 6H_2O$ in an amount of 1.4 mass % as catalyst in the presence of active carbon.

Reaction temperature: 60° C., hydrazine monohydrate: (80% product) 2 molar equivalents, solvent: EtOH (12 mass times)

HPLC relative area percentage: (3) 44.8%, (4) 51.2%, (5) 3.7%.

It is understood from the above-mentioned results that the method of the present invention effectively inhibits the formation of by-products and thereby provides aminobenzopyran compound in a very high yield. That is, it is understood that the method of the present invention confers a high reaction selectivity on the nitro group of 2,2-dimethyl 2H-1-benzopyran compound.

INDUSTRIAL APPLICABILITY

The present invention establishes a process for producing aminobenzopyran, by which the compound can be obtained in a high yield and which necessitates a simple post-treatment, results in little wastes and has no influence on reactors. Therefore, for example, the present invention can be utilized for the production of antifibrillatory agents or hypotensive agents for which the aminobenzopyran compound is used as intermediate.

The invention claimed is:

1. A method for producing aminobenzopyran compound of formula (2)

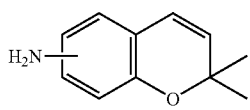

(2)

characterized by reducing a nitro group on 2,2-dimethyl 2H-1-benzopyran compound of formula (1)

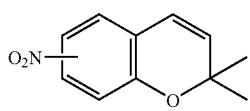

(1)

with hydrazine in the presence of platinum or palladium as a metal catalyst.

2. The method for producing aminobenzopyran compound according to claim 1, wherein the 2,2-dimethyl 2H-1-benzopyran compound of formula (1) is 2,2-dimethyl-6-nitro 2H-1-benzopyran of formula (3)

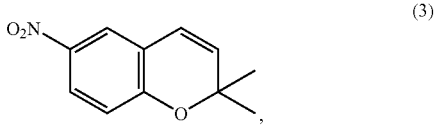

(3)

the aminobenzopyran compound of formula (2) is 6-amino-2,2-dimethyl 2H-1-benzopyran of formula (4)

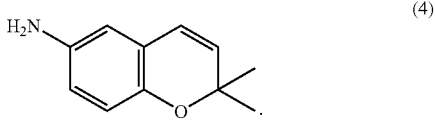

(4)

3. The method for producing aminobenzopyran compound according claim 1, wherein the metal in the metal catalyst is platinum.

4. The method for producing aminobenzopyran compound according to claim 1, wherein the hydrazine is used in an amount of 2 to 5 molar equivalents to 1 molar equivalent of 2,2-dimethyl 2H-1-benzopyran compound.

5. The method for producing aminobenzopyran compound according to claim 2, wherein the hydrazine is used in an amount of 2 to 5 molar equivalents to 1 molar equivalent of 2,2-dimethyl 2H-1-benzopyran compound.

6. The method for producing aminobenzopyran compound according to claim 3, wherein the hydrazine is used in an amount of 2 to 5 molar equivalents to 1 molar equivalent of 2,2-dimethyl 2H-1-benzopyran compound.

* * * * *